United States Patent
Arruda et al.

(10) Patent No.: US 9,670,267 B2
(45) Date of Patent: Jun. 6, 2017

(54) COMPOSITIONS AND METHODS FOR ENHANCING COAGULATION FACTOR VIII FUNCTION

(71) Applicant: The Children's Hospital of Philadelphia, Philadelphia, PA (US)

(72) Inventors: Valder Arruda, Philadelphia, PA (US); Rodney Camire, Sicklerville, NJ (US); Nicholas Iacobelli, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 45 days.

(21) Appl. No.: 14/468,108

(22) Filed: Aug. 25, 2014

(65) Prior Publication Data

US 2015/0056271 A1 Feb. 26, 2015

Related U.S. Application Data

(63) Continuation of application No. 13/437,486, filed on Apr. 2, 2012, now Pat. No. 8,816,054, which is a continuation of application No. PCT/US2010/051285, filed on Oct. 4, 2010.

(60) Provisional application No. 61/248,179, filed on Oct. 2, 2009.

(51) Int. Cl.
*C07K 14/755* (2006.01)
*C07H 21/04* (2006.01)
*A61K 38/37* (2006.01)
*A61K 48/00* (2006.01)
*A61K 38/00* (2006.01)

(52) U.S. Cl.
CPC ............ *C07K 14/755* (2013.01); *A61K 38/00* (2013.01)

(58) Field of Classification Search
None
See application file for complete search history.

(56) References Cited

U.S. PATENT DOCUMENTS

2004/0005670 A1 1/2004 High et al.

FOREIGN PATENT DOCUMENTS

CA 2 264 431 A1 9/1999

OTHER PUBLICATIONS

New England Biolabs Amino Acid Structures: 1 page; retrieved from the Internet Dec. 7, 2013.
Osterberg, T., et al., B-Domain Deleted Recombinant Factor VIII Formulation and Stability, Seminars in Hematology, 2001, 38(2):40-43.
Sabatino, D.E., et al., Recombinant Canine B-Domain-Deleted FVIII Exhibits High Specific Activity and is Safe in the Canine Hemophilia A Model, Blood, 2009, 114(20):4562-5.
Siner, J., et al., Bioengineering Factor VII B-Domain Sequences Improves Function and Efficacy in Hemophilia A Models, Blood, 2012, 120(21): Abstract 2208.

*Primary Examiner* — Marsha Tsay
(74) *Attorney, Agent, or Firm* — Pillsbury Winthrop Shaw Pittman LLP; Robert M. Bedgood

(57) ABSTRACT

Factor VIII variants and methods of use thereof are disclosed.

14 Claims, 20 Drawing Sheets cFVIII-BDD (single chain)
cFVIII-BDD (two chain)
cFVIIIa
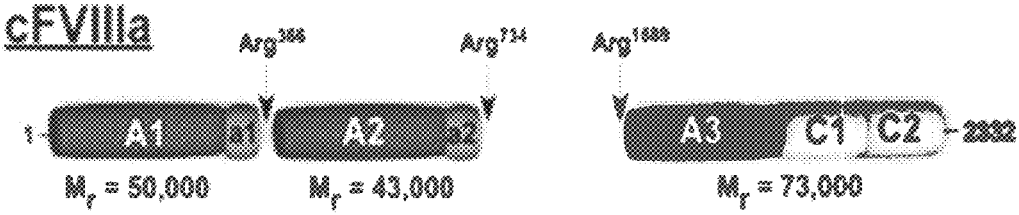
Figure 2A

| Hemophilia A Dog | # of Dogs | Previous Exposure to Normal Canine Plasma | Canine Protein | Dose; # of infusions | Anti-cFVIII IgG | Bethesda Titer |
|---|---|---|---|---|---|---|
| Adult (6-9 y.o.) | 2 | + | Recombinant BDD | 2.5 µg/kg; 5 infusions | No | No |
| Neonates | 3 | - | Recombinant BDD | 2 µg/kg; 15 infusions | No | No |
| | 2 | - | Plasma Derived | 50cc plasma; 8 infusions | No | No |

Figure 11: Injury at the carotid artery induced by FeCl3
3 minute observation
2 minute injury (15% FeCl3)
time = 0, observe for 30 minutes

| Mouse | AAV vector treatment | FVIII antigen ng/ml | Clot Stability transient/stable | Time to full occlusion time to occlusion (minutes) |
|---|---|---|---|---|
| 2-2 | wt | 120.8 | stable | 12.25 |
| 4-1 | wt | 73.1 | transient | 20.25 |
| 5-2 | wt | 74.9 | transient | 6.75 |
| 6 (540) | wt | 87 | stable | 12.67 |
| 4B | RH | 171 | stable | 8.43 |
| 5 | RH | 145 | stable | 7.5 |
| 4A | RH | 143.7 | stable | 8.5 |
| 6-2 | pbs | 0 | none | >30 |
| WT | --- | --- | stable | 11.33 |

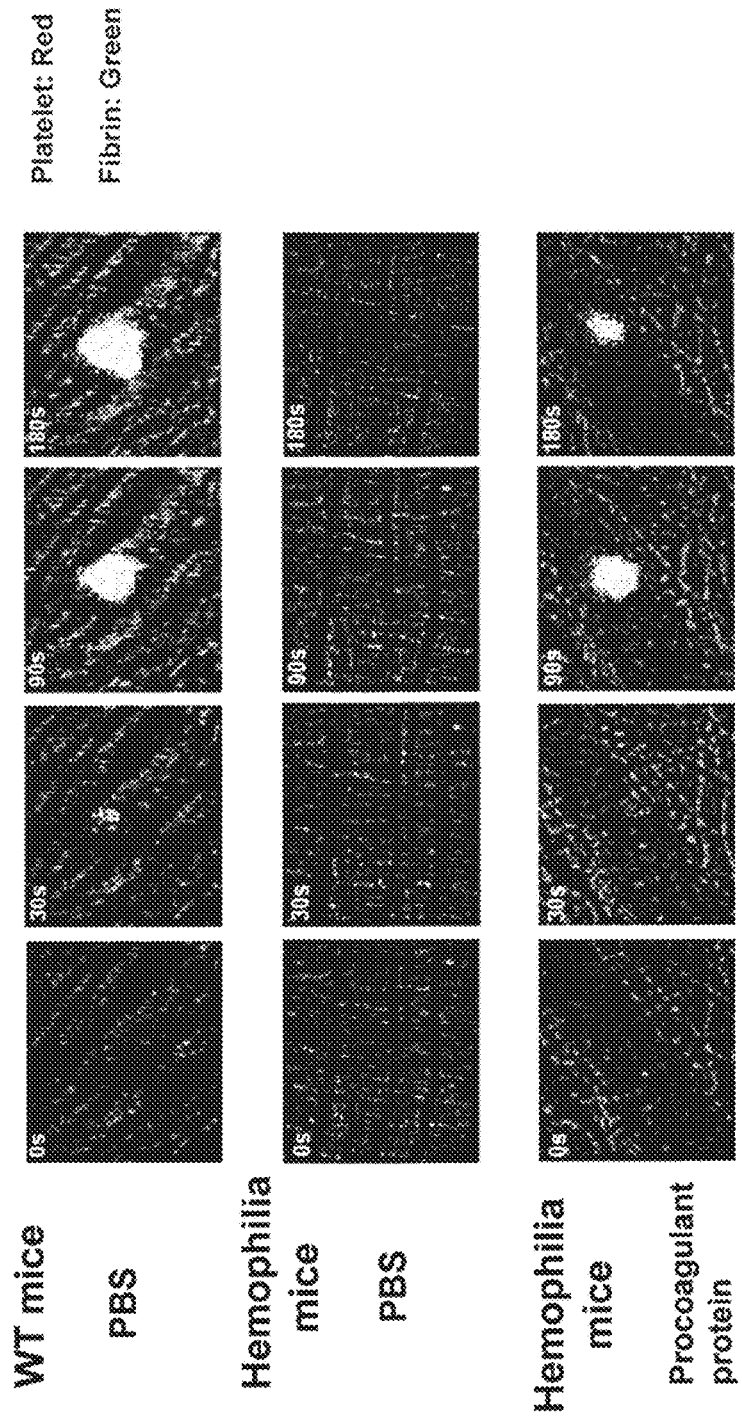
Figure 12A: Model, Laser-induced thrombus formation

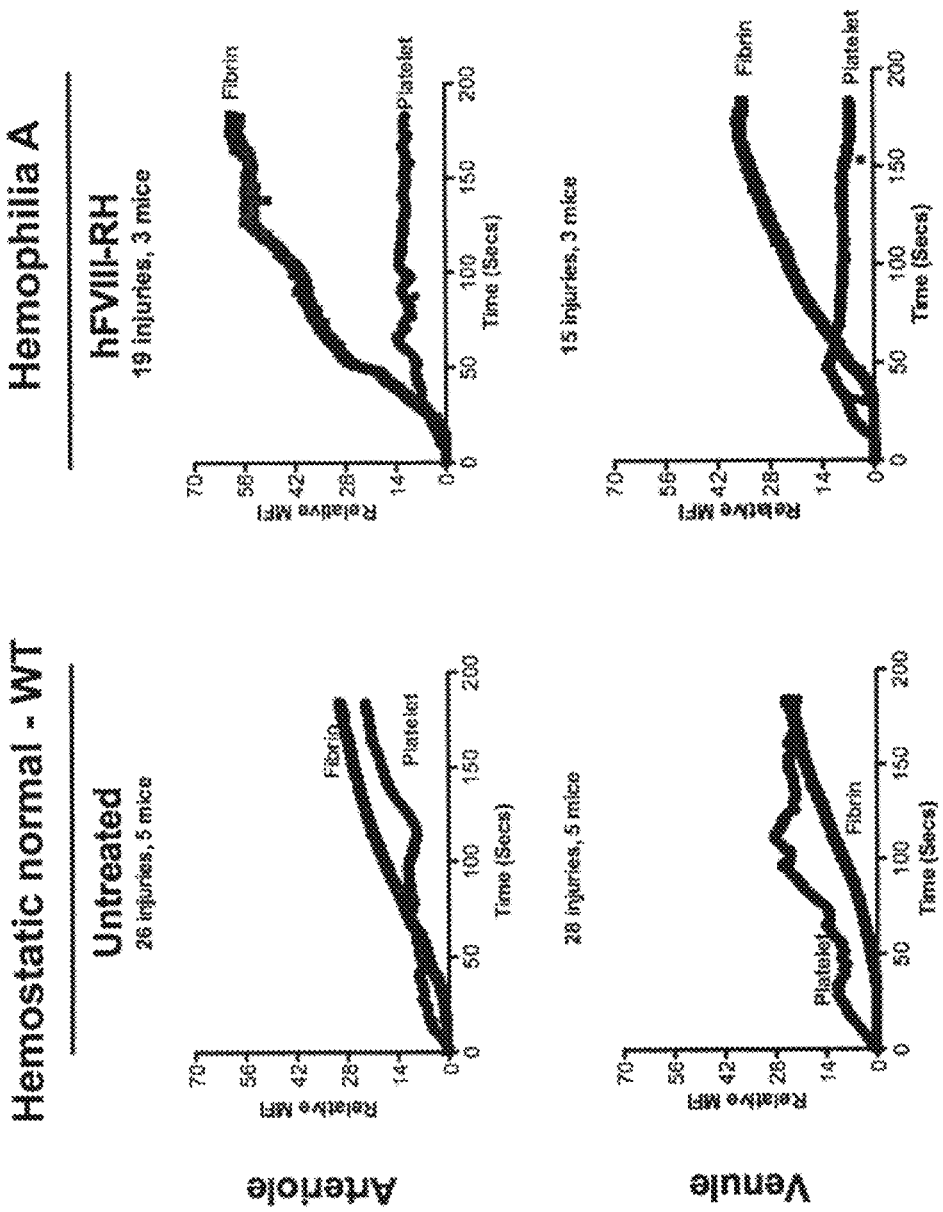

COMPOSITIONS AND METHODS FOR ENHANCING COAGULATION FACTOR VIII FUNCTION

This application is a continuation of U.S. patent application Ser. No. 13/437,486 filed Apr. 2, 2012, now U.S. Pat. No. 8,816,054, which is a continuation of PCT/US2010/51285 filed Oct. 4, 2010 which in turn claims priority to 61/248,179 filed Oct. 2, 2009, each of the aforementioned applications being incorporated by reference herein.

FIELD OF THE INVENTION

The present invention relates to the fields of medicine and hematology. More specifically, the invention provides novel coagulation Factor VIII agents and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

Hemophilia A (HA) is an X-linked bleeding disease resulting from a functional FVIII deficiency, affecting 1:5000 males worldwide. For several decades the HA dog model has been the most extensively used for preclinical studies (1), Notably, in two strains of dogs the underlying mutation consists of an inversion in intron 22 of the FVIII gene that is analogous to the most common human mutation (2). This model faithfully replicates the human disease at both genotypic and phenotypic levels (3,4). To date there is no characterization of the cFVIII protein due to difficulties in purifying large amounts from canine plasma and to the relative poor performance in recombinant FVIII expression systems in general. Although the cFVIII cDNA sequence has a high sequence identity to human FVIII (hFVIII) (5), adult HA dogs develop immune responses upon exposure to hFVIII that preclude the assessment of the efficacy and safety of potential novel therapies for HA. Notably, among humans even small nucleotide changes in the hFVIII gene may predispose to inhibitor formation (6).

Identifying hFVIII variants that exhibit superior coagulation properties are highly desirable. It is an object of the invention to provide such proteins for use as therapeutics.

SUMMARY OF THE INVENTION

Thus, in accordance with the present invention, a Factor VIII (FVIII) variant which exhibits improved capacity to modulate hemostasis is provided. In a preferred embodiment, the variant FVIII is a human variant, lacking most of the B domain (BDD=B domain deleted), comprising a R1645H amino acid substitution which exhibits increased specific activity and stability relative to human FVIII-BDD lacking said substitution. In yet another embodiment, variants comprising further deletions and modifications to the PACE/FURIN cleavage site are also within the scope of the invention. Also provided are nucleic acids encoding the variants described herein. Such nucleic acids are optionally cloned into an expression vector. Host cells comprising such expression vectors are also encompassed by the present invention.

In yet another aspect, a pharmaceutical composition comprising the Factor VIII variant described above in a biologically compatible carrier is provided.

The invention also provides a method for treatment of a hemostasis related disorder in a patient in need thereof, comprising administration of a therapeutically effective amount of the pro-coagulant variant FVIII described herein in a biologically acceptable carrier. Such disorders include, without limitation hemophilia A, hemophilia A with inhibitor, von Willebrand diseases, non-hemophilia subjects with inhibitors to FVIII, disorders of platelets, ADAMTS13-related diseases, bleeding associated with trauma, injury coagulopathy, and disseminated intravascular coagulation (DIC).

BRIEF DESCRIPTION OF THE DRAWINGS

FIG. 3. Canine FVIII-BDD is functional and does not induce an immune response in HA Dogs. FIG. 3C) Monitoring antibody and inhibitor formation to cFVIII-BDD in HA dogs. In addition to the adult dogs, neonatal naïve animals that had not previously been exposed to normal canine plasma were treated with cFVIII-BDD. IgG represets both IgG1 and IgG2 data.

FIG. 11: A table showing results from injury studies at the carotid artery induced by FeCl3. 3 minute observation; 2 minute injury (15% FeCl3) time=0, observe for 30 minutes.

FIG. 12: Data obtained using a laser induced thrombus model. FIG. 12A is reproduced from Ivanciu et al., Nat. Biotechnol (2011) and shows a laser induced thrombus formation model. FIG. 12C shows data obtained at the arteriole and the venule.

DETAILED DESCRIPTION OF THE INVENTION

Figure 1:
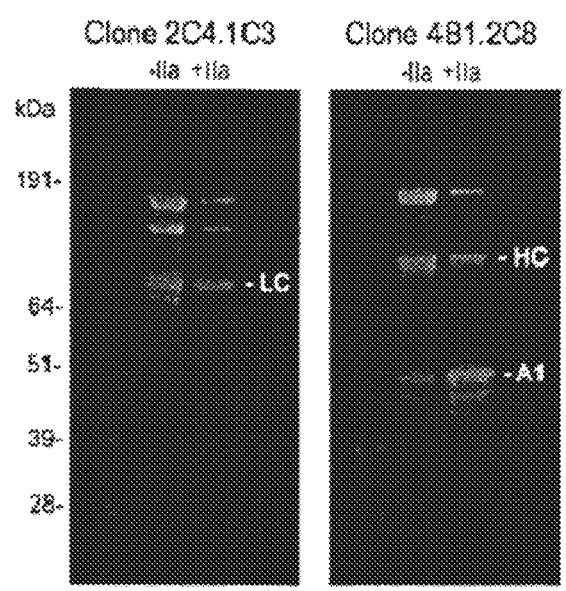
FIG. 1: Western blot analysis of cFVIII-BDD monoclonal antibodies. Monoclonal antibodies were screened by western blot using cFVIII-BDD and thrombin activated cFVIII-BDD to determine their specificity for the heavy chain (HC) or the light chain (LC). One microgram of cFVIII or activated cFVIII was loaded onto a reducing 4-12% NuPage gel with Seablue Plus 2 marker (Invitrogen, Carlsbad, Calif.), run at 200V for 50 minutes and transferred to a nitrocellulose membrane. cFVIII was detected using the mouse monoclonal antibody (4 μg/ml) followed by detection with IRDye 800CW rabbit anti-mouse IgG (H&L) (Rockland Immunochemicals, Inc. Gilbertsville, Pa.) and scanned on an Odyssey Infrared Imaging System (LI-COR Biosciences, Lincoln, Nebr.).

Production of recombinant B-domain deleted canine factor VIII (cFVIII-BDD) unexpectedly revealed superior protein yields with 3-fold increased specific activity and stability relative to human FVIII-BDD (hFVIII-BDD). The cFVIII-BDD is efficient at inducing hemostasis in human plasma containing FVIII inhibitors. Infusion of cFVIII-BDD in hemophilia A dogs resulted in correction of the disease phenotype with a pharmacokinetic profile similar to clinical experience with hFVIII-BDD. Notably, immune tolerance challenges with cFVIII-BDD in young and adult hemophilia A dogs did not induce the formation of neutralizing or non-neutralizing antibodies to cFVIII. These data indicate that the FVIII variant described herein should exhibit greater efficacy and safety in preclinical studies of new therapies for hemophilia A.

I. DEFINITIONS

Various terms relating to the biological molecules of the present invention are used hereinabove and also throughout the specification and claims.

The phrase "variant Factor VIII (FVIII)" refers to a modified FVIII which has been genetically altered such that the encoded protein exhibits a 3-fold increase in specific activity and enhanced stability when compared to unmodified FVIII. The nucleotide sequences described herein are readily obtainable from GenBank. For human FVIII, see Accession No. NG-011403.1. For canine FVIII, see Accession No. NM-001003212-1. cFVIII-BDD refers to a FVIII variant which lacks the B domain.

The phrase "hemostasis related disorder" refers to bleeding disorders such as hemophilia A, hemophilia A patients with inhibitory antibodies, deficiencies in coagulation Factors, VII, VIII, IX and X, XI, V, XII, II von Willebrand factor, combined FV/FVIII deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pore" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

II. PREPARATION OF VARIANT FVIII ENCODING NUCLEIC ACID MOLECULES AND POLYPEPTIDES

A. Nucleic Acid Molecules

Nucleic acid molecules encoding the variant FVIII molecules of the invention may be prepared by using recombinant DNA technology methods. The availability of nucleotide sequence information enables preparation of isolated nucleic acid molecules of the invention by a variety of means. For example, nucleic acid sequences encoding a variant FVIII polypeptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable E. coli host cell. Alternatively, the nucleic acids may be maintained in vector suitable for expression in mammalian cells. In cases where post-translational modification affects coagulation function, it is preferable to express the molecule in mammalian cells.

Variant FVIII-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting FVIII expression.

B. Proteins

A B-domain deleted FVIII polypeptide of the present invention may be prepared in a variety of ways, according to known methods. The protein may be purified from appropriate sources, e.g., transformed bacterial or animal cultured cells or tissues which express engineered FVIII by immunoaffinity purification.

The availability of nucleic acid molecules encoding a variant FVIII polypeptide enables production of FVIII using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis., or BRL, Rockville, Md.

Alternatively, according to a preferred embodiment, larger quantities of FVIII may be produced by expression in a suitable prokaryotic or eukaryotic expression system. For example, part or all of a DNA molecule encoding variant Factor VIII for example, may be inserted into a plasmid vector adapted for expression in a bacterial cell, such as E. coli or a mammalian cell such as CHO or Hela cells. Alternatively, in a preferred embodiment, tagged fusion proteins comprising FVIII can be generated. Such FVIII-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as E. coli or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant FVIII proteins, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

FVIII proteins, prepared by the aforementioned methods, may be analyzed according to standard procedures. For example, such proteins may be assessed for altered coagulation properties according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems.

III. USES OF FVIII PROTEINS AND FVIII-ENCODING NUCLEIC ACIDS

Variant FVIII nucleic acids encoding polypeptides having altered coagulation activities may be used according to this invention, for example, as therapeutic and/or prophylactic agents (protein or nucleic acid) which modulate the blood coagulation cascade or as a transgene in gene-, and or cell-based strategies for continuous expression of FVIII and its variants in hemophilia A patients. The present inventors have discovered modifications of FVIII molecules which result in increased coagulation activity and greater stability thereby effectively improving hemostasis.

A. Variant FVIII Polypeptides

In a preferred embodiment of the present invention, variant FVIII polypeptides may be administered to a patient via infusion in a biologically compatible carrier, preferably via intravenous injection. The variant FVIIIs of the invention may optionally be encapsulated into liposomes or mixed with other phospholipids or micelles to increase stability of the molecule. FVIII may be administered alone or in combination with other agents known to modulate hemostasis (e.g., Factor V, Factor Va or derivatives thereof). An appropriate composition in which to deliver FVIII polypeptides may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified FVIII analog contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the FVIII analog can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e. it can be allowed to stand in dissolved form for a prolonged time prior to application.

The preparation according to the present invention can be made available as a pharmaceutical preparation with FVIII activity in the form of a one-component preparation or in combination with other factors in the form of a multi-component preparation. Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

The pharmaceutical protein preparation may be used at dosages of between 30-100 IU/kg (One I.U is 100 ng/ml) at as single daily injection or up to 3 times/day for several days. Patients may be treated immediately upon presentation at the clinic with a bleed. Alternatively, patients may receive a bolus infusion every eight to twelve hours, or if sufficient improvement is observed, a once daily infusion of the variant FVIII described herein.

B. FVIII-Encoding Nucleic Acids

FVIII-encoding nucleic acids may be used for a variety of purposes in accordance with the present invention. In a preferred embodiment of the invention, a nucleic acid delivery vehicle (i.e., an expression vector) for modulating blood coagulation is provided wherein the expression vector comprises a nucleic acid sequence coding for a variant FVIII polypeptide, or a functional fragment thereof as described herein. Administration of FVIII-encoding expression vectors to a patient results in the expression of FVIII polypeptide which serves to alter the coagulation cascade. In accordance with the present invention, an FVIII encoding nucleic acid sequence may encode an FVIII polypeptide as described herein whose expression increases hemostasis. In a preferred embodiment, a FVIII nucleic acid sequence encodes a human FVIII polypeptide variant.

Expression vectors comprising variant FVIII nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible compositions.

In a preferred embodiment of the invention, the expression vector comprising nucleic acid sequences encoding the variant FVIII variants is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-1 to AAV-12, and others) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, retroviral vectors, lentiviral vectors, non-viral vectors and others.

In a preferred embodiment of the present invention, methods are provided for the administration of a viral vector comprising nucleic acid sequences encoding a variant FVIII, or a functional fragment thereof. AAV vectors and lentiviral vectors have broad utility in the methods of the present invention and preferably do not include any viral genes associated with pathogenesis. Most preferably, only the essential parts of vector e.g., the ITR and LTR elements, respectively are included. Direct delivery of vectors or ex-vivo transduction of human cells and followed by infusion into the body will result in expression of variant FVIIIs thereby exerting a beneficial therapeutic effect on hemostasis. In the context of the variant Factor VIII described herein, such administration enhances pro-coagulation activity.

Recombinant AAV and lentiviral vectors have found broad utility for a variety of gene therapy applications. Their utility for such applications is due largely to the high efficiency of in vivo gene transfer achieved in a variety of organ contexts.

AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting retinal epithelium, liver, skeletal muscle, airways, brain, joints and hematopoietic stem cells. It is likely that non-viral vectors based on plasmid DNA or minicircles will be also suitable gene transfer vectors for a large gene as that encoding FVIII.

It is desirable to introduce a vector that can provide, for example, multiple copies of a desired gene and hence greater amounts of the product of that gene. Improved AAV and lentiviral vectors and methods for producing these vectors have been described in detail in a number of references, patents, and patent applications, including: Wright J. F. (Hum Gene Ther 20:698-706, 2009) which is the technology used for the production of clinical grade vector at our facility at Children's Hospital of Philadelphia. Lentiviral vector can be produced at CHOP and the other vectors are available through the Lentivirus vector production core laboratory by NHLBI Gene Therapy Resource Program (GTRP)—Lentivirus Vector Production Core Laboratory. For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant FVIIIs or functional fragments thereof. For example, nucleic acid sequences encoding variant FVIII under the control of a cytomegalovirus (CMV) promoter can be employed for skeletal muscle expression or the hAAT-ApoE and others for liver specific expression. Hematopoietic specific promoters in lentiviral vectors may also be used to advantage in the methods of the present invention.

Exemplary Methods for Producing AAV Vectors

AAV for recombinant gene expression have been produced in the human embryonic kidney cell line 293 and extensively recently reviewed by the Director of Clinical Vector Core at CHOP, Dr. J. F. Wright (Hum Gene Ther 20:698-704 2009). Briefly, AAV vectors are engineered from wild-type AAV, a single-stranded DNA virus that is non-pathogenic. The parent virus is non-pathogenic, the vectors have a broad host range, and they can infect both dividing and non-dividing cells. The vector is engineered from the virus by deleting the rep and cap genes and replacing these with the transgene of interest under the control of a specific promoter. For recombinant AAV preparation, the upper size limit of the sequence that can be inserted between the two ITRs is ~5.0 kb. The plasmids expressing canine or human FIX under the control of the CMV promoter/enhancer and a second plasmid supplying adenovirus helper functions along with a third plasmid containing the AAV-2 rep and cap genes were used to produce AAV-2 vectors, while a plasmid containing either AAV-1, AAV-6, or AAV-8 cap genes and AAV-2 rep gene and ITR's are used to produce the respective alternate serotype vectors (Gao et al., (2002) Proc. Natl Acad. Sci. USA 99:11854-11859; Xiao et al., (1999) J. Virol. 73:3994-4003; Arruda et al., (2004) Blood 103:85-92). AAV vectors are purified by repeated CsCl density gradient centrifugation and the titer of purified vectors determined by quantitative dot-blot hybridization. Vectors used for experiments in dogs and mice presented herein were prepared by the Vector Core at The Children's Hospital of Philadelphia.

Also included in the present invention is a method for modulating hemostasis comprising providing cells of an individual with a nucleic acid delivery vehicle encoding a variant FVIII polypeptide and allowing the cells to grow under conditions wherein the FVIII polypeptide is expressed.

From the foregoing discussion, it can be seen that FVIII polypeptides, and FVIII polypeptide expressing nucleic acid vectors may be used in the treatment of disorders associated with aberrant blood coagulation.

C. Pharmaceutical Compositions

The expression vectors of the present invention may be incorporated into pharmaceutical compositions that may be delivered to a subject, so as to allow production of a biologically active protein (e.g., a variant FVIII polypeptide or functional fragment or derivative thereof) or by inducing continuous expression of the FVIII transgene in vivo by gene- and or cell-based therapies or by ex-vivo modification of the patient's or donor's cells. In a particular embodiment of the present invention, pharmaceutical compositions comprising sufficient genetic material to enable a recipient to produce a therapeutically effective amount of a variant FVIII polypeptide can influence hemostasis in the subject. Alternatively, as discussed above, an effective amount of the variant Factor VIII polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable exeipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of FVIII-containing vectors or polypeptides, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant FVIII polypeptide. Thus, a therapeutically effective amount in humans will fall in a relatively broad range that may be determined by a medical practitioner based on the response of an individual patient to vector-based FVIII treatment.

D. Administration

The variant Factor VIII polypeptides, alone or in combination with other agents may be directly infused into a patient in an appropriate biological carrier as described hereinabove. Expression vectors of the present invention comprising nucleic acid sequences encoding variant FVIII, or functional fragments thereof, may be administered to a patient by a variety of means (see below) to achieve and maintain a prophylactically and/or therapeutically effective level of the FVIII polypeptide. One of skill in the art could readily determine specific protocols for using the FVIII encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

Variant FVIII encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising FVIII nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant FVIII polypeptide.

Also provided are lentivirus or pseudo-typed lentivirus vectors comprising a nucleic acid sequence encoding a variant FVIII polypeptide.

Also encompassed are naked plasmid or expression vectors comprising a nucleic acid sequence encoding a variant FVIII polypeptide.

The following materials and methods are provided to facilitate the practice of Example I.

Purification of Canine and Human FVIII-BDD:

Plasmids encoding hFVIII-BDD or cFVIII-BDD were introduced into baby hamster kidney (BHK) cells and high producing stable clones were established as described using standard techniques (Toso et al. (2004) J. Biol. Chem. 279:21643-21650). Cells were expanded into triple flasks and cultured in DMEM/F12 media (no phenol red) supplemented with ITS, 2.5 mM $CaCl_2$ and 1.0 mg/mL Albumax (Invitrogen, Carlsbad, Calif.). Variants of FVIII containing amino acid substitutions were generated using site directed mutagenesis. Conditioned media was collected daily for 4-6 days, centrifuged, and inhibitors added (10 µM APMSF and 1 mM benzamidine). For purification, media was processed daily and loaded onto a ~70 mL SPSepharose FF column (Amersham Biosciences, Piscataway, N.J.) equilibrated in 20 mM MES, 0.15 M NaCl, 5 mM $CaCl_2$, 0.01% Tween-80, pH 6.8. The column was washed with the same buffer and eluted with 20 mM MES, 0.65 M NaCl, 5 mM $CaCl_2$, 0.01% Tween-80, pH 6.8. Fractions containing cFVIII-BDD (monitored by clotting assay) were stored at −80° C. Following successive daily runs of the SP-Sepharose column, all fractions containing activity were pooled and diluted with 20 mM MES/5 mM CaCl2/0.01% Tween-80, pH 6.8 and then loaded on a Poros HS/20 column (10×100 mm; Applied Biosystems, Foster City, Calif.) equilibrated with the same buffer. The column was washed with 20 mM MES, 2 mM $CaCl_2$, pH 6.0 and then eluted with a 0-1.0 M NaCl gradient, cFVIII-BDD containing fractions were pooled, and then and diluted with 20 mM HEPES/5 mM CaCl2, pH 7.4 and then loaded on a Poros HQ/20 column (4.6×100 mm; Applied Biosystems, Foster City, Calif.) equilibrated with the same buffer. The column was washed with 20 mM HEPES/5 mM CaCl2, pH 7.4 and then eluted with a 0-65 M NaCl gradient. Fractions containing activity were dialyzed versus 20 mM Hepes, 2 mM CaCl2, pH 7.4 for 2 hr and the protein was stored at −80° C. in small aliquots.

Protein specific activity was determined by activated partial thromboplastin time (aPTT) with minor modifications (12). Decay of activated FVIII activity was monitored by purified component assay using both reconstituted human factor Xase complex and plasma models as previously described (11). N-terminal sequencing was determined in the laboratory of Dr. Alexander Kurosky and Dr. Steven Smith, at UTMB (Galveston, Tex.). Enzymatic cleavage of N-linked glycans was carried out using recombinant N-glycosidase F (Boehringer Mannheim, Indianapolis, Ind.) as reported before (13).

cFVIII-BDD Antigen ELISA cFVIII-BDD protein was used for the generation of a series of rabbit anti-cFVIII-BDD polyclonal and murine monoclonal anticFVIII-BDD antibodies (Green Mountain Antibodies, Burlington, Vt.) (See FIG. 1). Anti-cFVIII antibodies were detected by Bethesda assay (14) or by cFVIII-specific IgG antibodies by ELISA. A monoclonal antibody to the light chain (clone 2C4.1C3) or heavy chain (clone 4B1.2C8) to capture the protein (2 µg/mL) followed by a rabbit anti-cFVIII-BDD polyclonal as a secondary antibody (2 µg/mL). The cFVIII-BDD was detected with a goat anti-rabbit antibody conjugated to horseradish peroxidase at a dilution of 1:15,000 (Jackson ImmunoResearch Laboratories, Inc., West Grove, Pa.). The standard curve was generated using serial dilution of recombinant cFVIII-BDD. Half-life and recovery were calculated as previously described. (15, 16).

Anti-cFVIII Specific IgG ELISA

ELISA was used to detect cFVIII-specific IgG antibodies by using purified cFVIII-BDD protein (1 μg/mL) to capture IgG1 or IgG2 antibodies in dog serum. Canine reference serum (Bethyl Laboratories Inc., Montgomery, Tex.) with known concentrations of IgG1 and IgG2 was used as a standard by coating with serial dilutions of the canine serum. Canine serum samples were diluted in LowCross-Buffer (Candor Bioscience GmbH, Germany). The IgG was detected with goat anti-canine IgG1 conjugated to horseradish peroxidase or sheep anti-canine IgG2 conjugated to horseradish peroxidase (Bethyl Laboratories Inc., Montgomery, Tex.) diluted 1:1000 in LowCross-Buffer (Candor, Bioscience GmbH, Weissensberg, Germany).

The following examples are provided to illustrate certain embodiments of the invention. They are not intended to limit the invention in any way.

Example 1

Figure 2B:
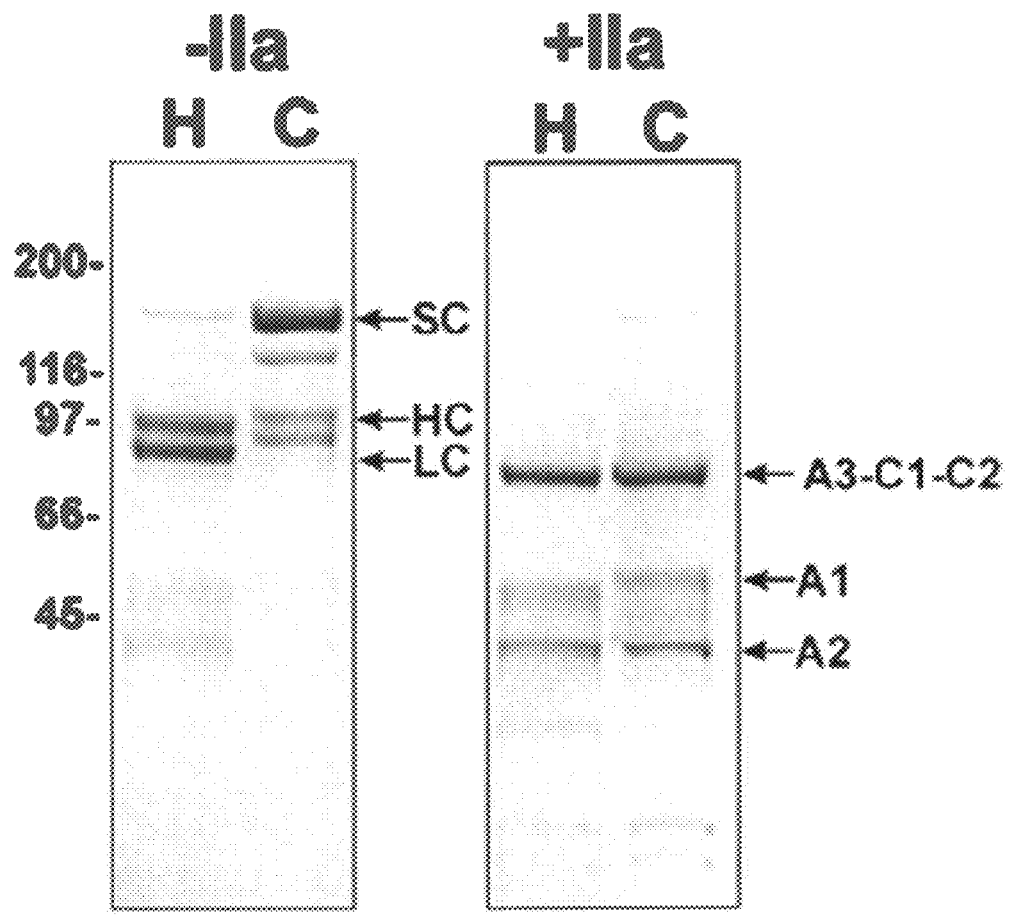
(FIG. 2B) Protein purity was assessed by loading 4 μg of human FVIII-BDD (H) and cFVIIIBDD (C) on a reducing SDS-PAGE followed by staining with Comassie blue (left; −IIa). FVIII-BDD (H or C; 800 nM) were incubated with IIa (+IIa; 5 nM) for 10 min and the resulting activated FVIII was run on a reducing SDS-PAGE (right, +IIa). The various domains of FVIII are indicated: SC: single chain, HC: heavy chain, LC: light chain, A3-C1-C2 (73 kDa), A1 (50 kDa), and A2 (43 kDa) (FIG. 2C) The specific activity of cFVIII-BDD and hFVIII-BDD were compared using a one- or two-stage aPTT in human deficient plasma. For the two stage assay (+IIa), FVIIIBDD (human or canine; 20 nM) in 20 mM Hepes/150 mM NaCl/5 mM $CaCl_2$/0.01% Tween 80, pH 7.4 (assay buffer) were intentionally activated with IIa (40 nM) for 30 sec at 25° C. Activated FVIII was immediately diluted into assay buffer with 0.1% albumin and then subsequently added to the aPTT clotting assay. In either the one- (−IIa) or two-stage aPTT (+IIa) the specific activity of cFVIII-BDD was 3-fold higher than hFVIII-BDD. The activation quotient was 22 for cFVIII and 28 for hFVIII.
Figure 2C:
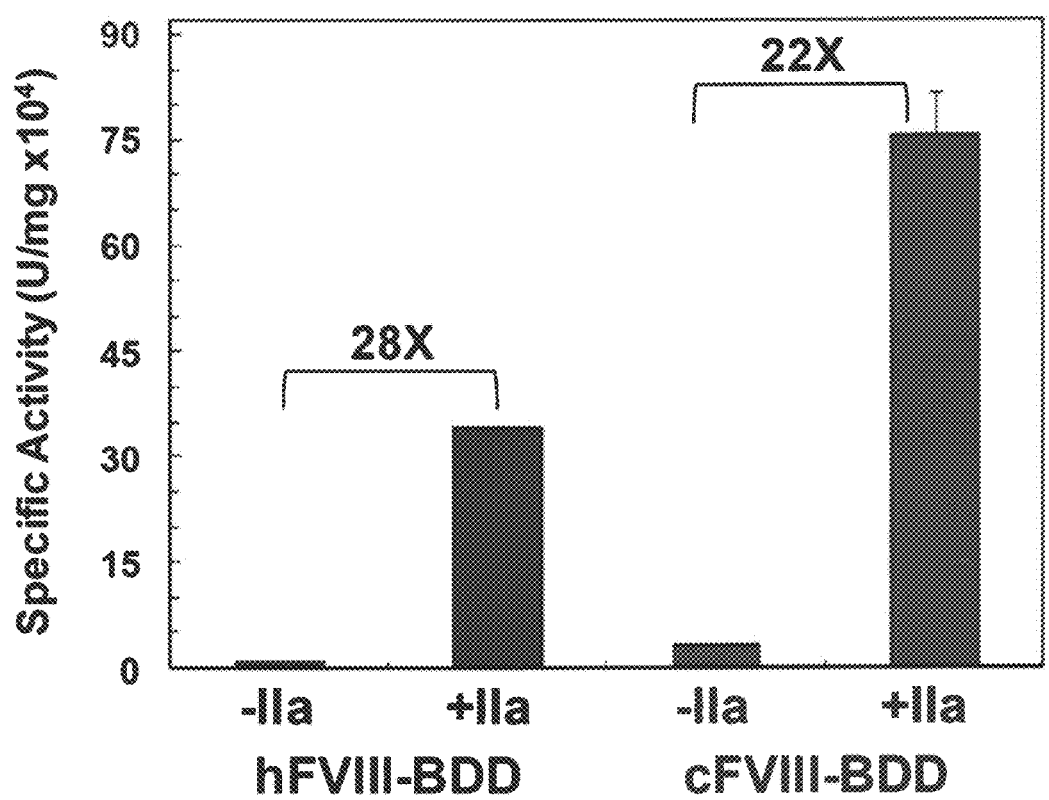
FIG. 2: Biochemical characterisation of FVIII-BDD.
(FIG. 2A) Canine (c) FVIII-BDD is predominantly synthesized as a 160 kD single chain protein with a smaller proportion being processed as a heterodimer. Thrombin (IIa) cleaves cFVIIIBDD at the indicated sites to yield activated cFVIII.
(FIG. 2D) A purified Xase assay was used to assess A2 domain stability. The Xase assay was performed by activating 20 nM cFVIII-BDD or hFVIII-BDD with 40 nM IIa for 30 seconds at 25° C. The reaction was stopped by adding 60 nM hirudin. At various time points after activation, FVIIIa (0.2 nM, final) was added to the Xase complex [hFIXa (2 nM), hFX (300 nM) and phospholipids (20 μM, phosphatidylcholine/phosphatidylserine; 75:25] and activation was measured by monitoring FXa generation using a chromogenic substrate.
Figure 2D:
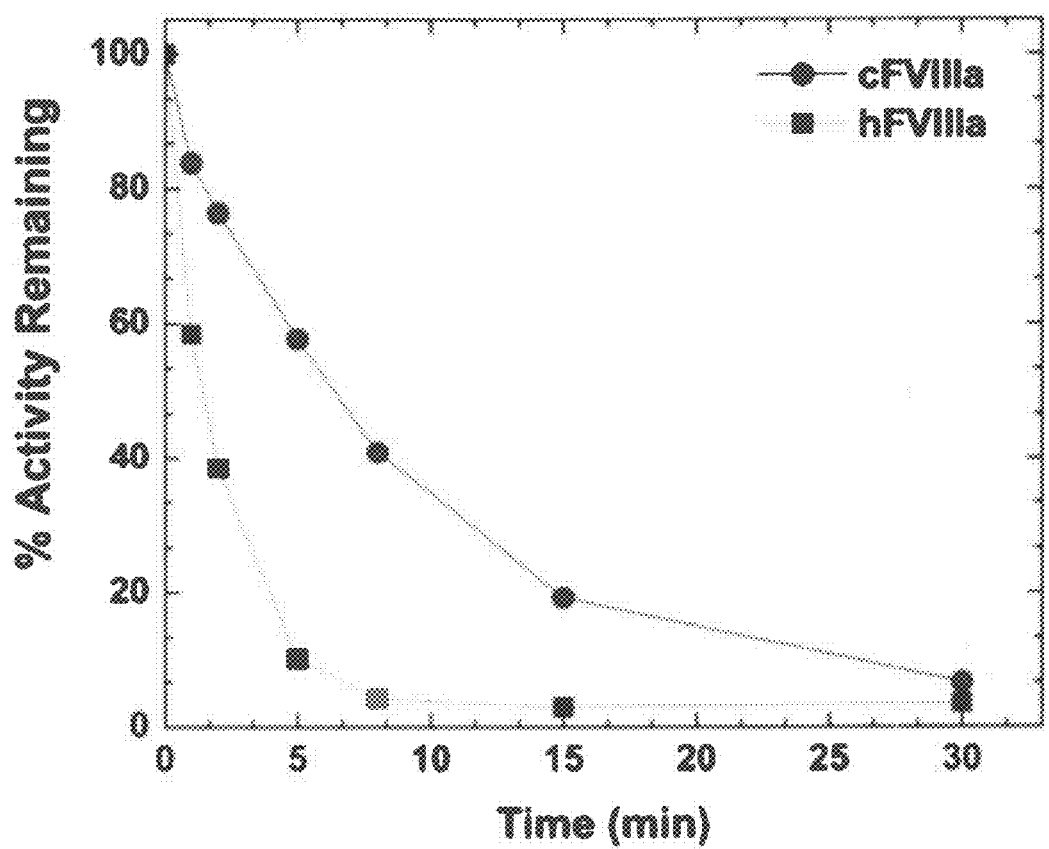

Recombinant Canine B-Domain Deleted FVIII Exhibits High Specific Activity and is Safe in the Canine Hemophilia A Model Using identical expression systems, we found that cFVIII-BDD typically yields 0.5 mg/L which is 3-fold higher than hFVIII-BDD (0.16 mg/L). Notably, purified cFVIII-BDD existed predominantly as a single-chain protein (>75% of total) whereas, as expected, hFVIII-BDD was primarily a heterodimer (FIG. 2A, B). The amino acid recognition sequence for the PACE/furin in cFVIII (HHQR)(17) differs from human and porcine FVIII (RHQR) and may explain the predominant single-chain form of cFVIII (17). Following treatment with thrombin cFVIII-BDD was properly activated and no major differences were observed between hFVIII-BDD and cFVIII-BDD (FIG. 2B). The A1 domain migration pattern differs between both FVIII species. However, removal of N-linked glycan resulted in similar migration of the A1 domains (data not shown). These data indicate that either the glycosylation structure on the A1 domains is different or that possibly only one site in the human A1 domain is glycosylated. Moreover, N-terminal sequencing of relevant band yields the expected results (data not shown). Using a one-stage aPTT, the specific activity cFVIII-BDD (33,926±675 U/mg) was ~3-fold higher than hFVIII-BDD (12,345±787 U/mg) (p<0.001). Similar findings were obtained after thrombin activation of canine and human FVIII in the two-stage aPTT (756,754±60,592 vs. 343,066±2090 U/mg, p<0.003) yielding an activation quotient (AQ) of 28 and 22 for human and canine, respectively (FIG. 2, panel C). Typically, low AQ represents contamination with activated forms of the protein and results in false high protein activity. These findings were consistent using three separate cFVIII-BDD preparations. Taken together these data using purified FVIII protein support the conclusions that cFVIII has an elevated intrinsic specific activity.

Following activation, FVIIIa rapidly loses activity due to A2-domain dissociation from the A1/A2/A3-C1-C2 heterotrimer. Purified cFVIII-BDD or hFVIII-BDD were rapidly activated (~30s) with thrombin and residual cofactor activity was monitored over time. Using either a purified component assay (FIG. 2, panel D) or clotting assay (data not shown) we found that the half-life of cFVIII was 3-fold longer than hFVIII. These findings suggest that cFVIIIa exhibits increased affinity for the A2-domain compared to hFVIIIa. While these data could, in part, account for the high specific activity of cFVIII, both porcine (17) and murine FVIIIBDD (11) also have enhanced A2-domain stability compared to hFVIII but apparently have equivalent specific activity to hFVIII. Thus, it is possible that the increased specific activity of cFVIII is due the single chain protein with higher stability.

To test the efficacy and safety of the cFVIII-BDD, we injected a series of adult and neonate HA dogs. In these dogs, no circulating FVIII antigen was detected, which is consistent with humans with the analogous FVIII mutation. In normal dogs cFVIII levels are 80-130 ng/mL which is comparable to human levels (100-200 ng/mL) and to cFVIII levels previously described (18).

Figure 3A:
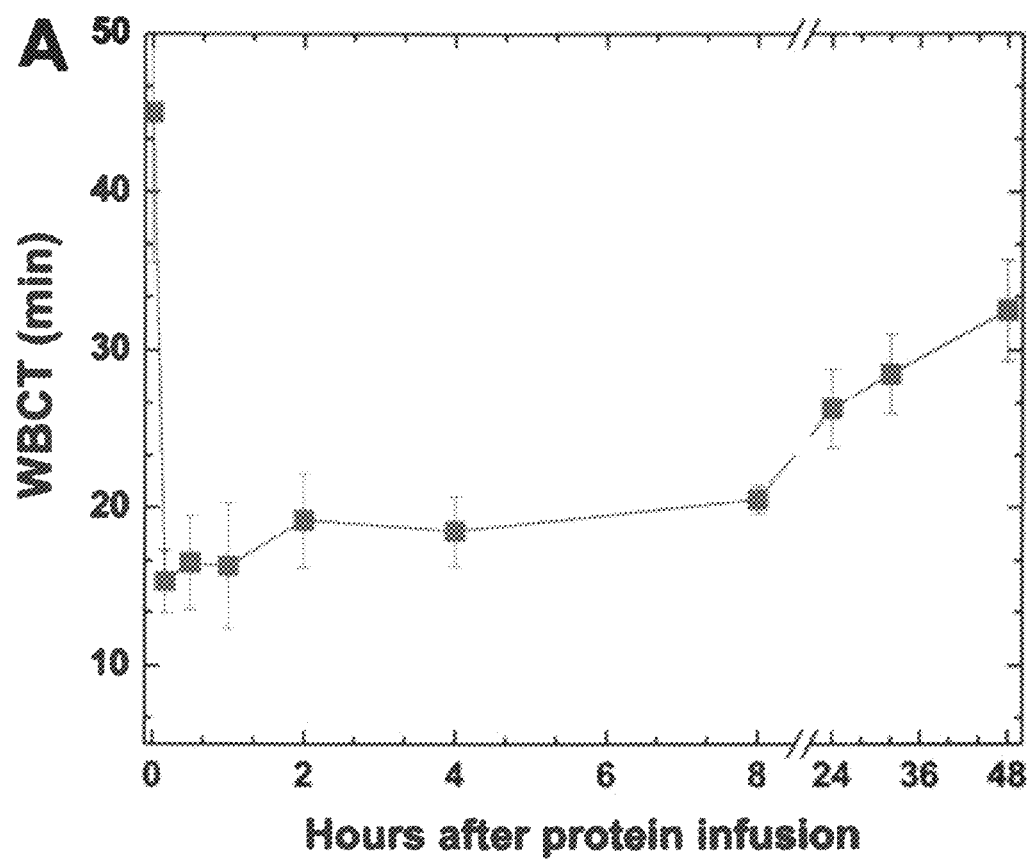
FIG. 3A) Whole blood clotting time (WBCT) following three injections of cFVIII-BDD in an HA dog (mean±SD). The WBCT shortened within 5 minutes of the protein infusion from >45 minutes (baseline) to 13-16.5 min (normal range: 8-12 min).
Figure 3B:
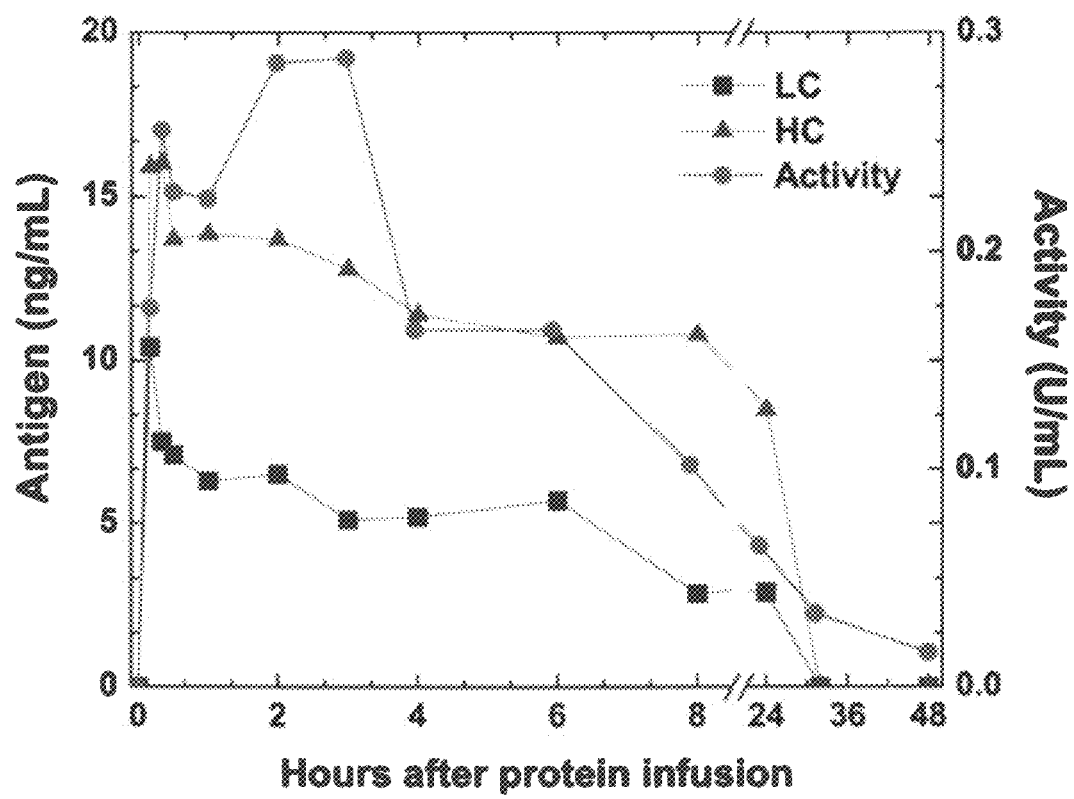
FIG. 3B) FVIII antigen (blue lines) and clotting activity (red line) following IV injection of cFVIII-BDD. For one protein infusion of the same dog, cFVIII activity was determined by Coatest assay and antigen levels were determined by ELISA specific for the cFVIII heavy (HC) or light chain (LC). The Coatest was performed using purified cFVIII as a standard. One unit is defined as 100 ng/ml.

HA dogs received cFVIII-BDD at doses of 2.5 μg/kg every 30 days for 2-4 months and serial plasma samples were collected through four weeks after each protein injection. cFVIIIBDD was functional as evidenced by the shortening of the whole blood clotting time (WBCT) and increased cFVIII clotting activity (FIG. 3). The recovery of the protein measured at 5-10 minutes (n=5 infusions) post-injection was excellent, reaching levels of 71.8%±9.2%. There was a good correlation between cFVIII activity and antigen levels (FIG. 3B). The levels of cFVIII slowly declined after the infusion and returned to baseline within 48-56 hours with a calculated half-life of 12-14 hours. There was no local or systemic toxicity and no evidence of pathological activation of coagulation. Together these data demonstrate that cFVIII-BDD is safe and efficacious in inducing sustained hemostasis in vivo and has a protein half-life comparable to the pharmacokinetics of hFVIII-BDD in HA dogs and from clinical experience in humans (19).

The use of these outbred immunocompetent HA dogs provide an ideal model to test the immunogenicity of cFVIII-BDD protein in both naïve neonates and adult dogs previously exposed to plasma-derived cFVIII. Those dogs do not develop antibody to cFVIII upon infusion of plasma-derived cFVIII. Here, in adult dogs, no antibodies to cFVIII-BDD were detected by Bethesda assay or cFVIII-specific IgGs after repetitive exposure to the protein (FIG. 3C). Furthermore, neonate dogs (n=3) exclusively exposed to cFVIII-BDD or small amounts of plasma-derived FVIII (n=2) also did not develop antibodies to cFVIII. In an HA dog with an inhibitor to plasma-derived cFVIII, inhibitor titers of 4 B.U. corresponds to 3000-4000 ng/mL of IgG2. These data are in contrast to the strong immune responses of adult HA dogs to hFVIII characterized by long-lasting antibody to hFVIII after exposure to the protein or following delivery of hFVIII gene or cell-based therapies (1, 16, 49, 20). Thus, cFVIII-BDD presents no immmunogenicity in this pivotal HA dog model which is essential for determining long-term efficacy and safety of novel therapeutic strategies for HA.

Figure 4:
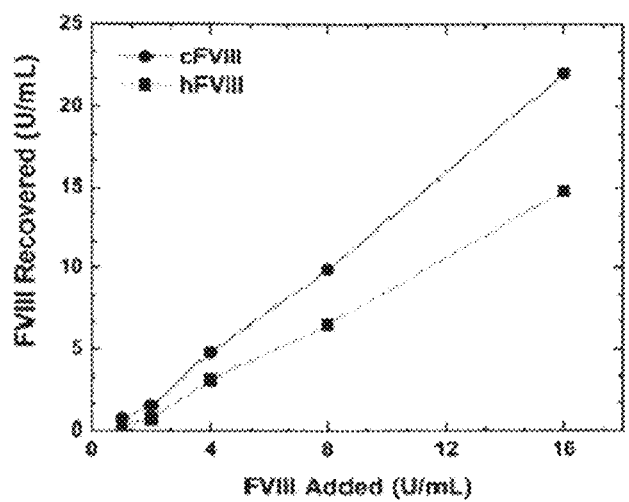
FIG. 4. Recovery of FVIII after exposure to anti-hFVIII antibodies. Different concentrations of cFVIII-BDD or hFVIII-BDD were incubated with human plasma containing hFVIII-specific neutralizing antibodies (11 B.U.) (George King Biomedical, Inc., Overland Park, Kans.) and residual FVIII activity was measured either immediately or after incubation at 37° C. for 2 hours. One unit is defined as 100 ng/mL.

We sought to compare the rates of inactivation of cFVIII-BDD with hFVIII-BDD in human plasma containing inhibitors to FVIII. The recovery of cFVIII after incubation with inhibitors was 40-45% higher than hFVIII (See FIG. 4). The higher survival of cFVIII in the presence of human inhibitors further supports the investigation of cFVIII as a potential bypass strategy for hemophilia.

The recombinant expression of cFVIII-BDD allowed us to generate large amounts of protein (>20 mg), develop valuable antibodies and begin to unravel intrinsic properties of the protein that may impact the development of treatment of hemophilia. The enhanced biological activity of cFVIII could partially result from the secretion of cFVIII as a single-chain protein and hFVIII variants with canine PACE/furin cleavage sites may help define whether these modifications would improve production and stability of the recombinant protein. Furthermore a detailed analysis of Xase complex assembly in kinetic characterization with canine FVIIIa will shed light on its apparent increased specific activity compared to hFVIII.

The efficacy and safety data from studies on non-inhibitor prone HA dogs demonstrate that cFVIII-BDD is an attractive option for the treatment of bleeds and for prophylaxis in dogs during complex or invasive procedures. The ability to detect non-neutralizing IgG antibodies in addition to neutralizing antibodies provides the opportunity to elucidate conflicting findings in gene or cell-based therapy in these dogs (21-24). A more comprehensive phenotypic characterization of the HA dogs is now feasible and further improves the relevance of preclinical studies for a new generation of gene- and cell-based therapies for hemophilia.

Example 2

Figure 5:
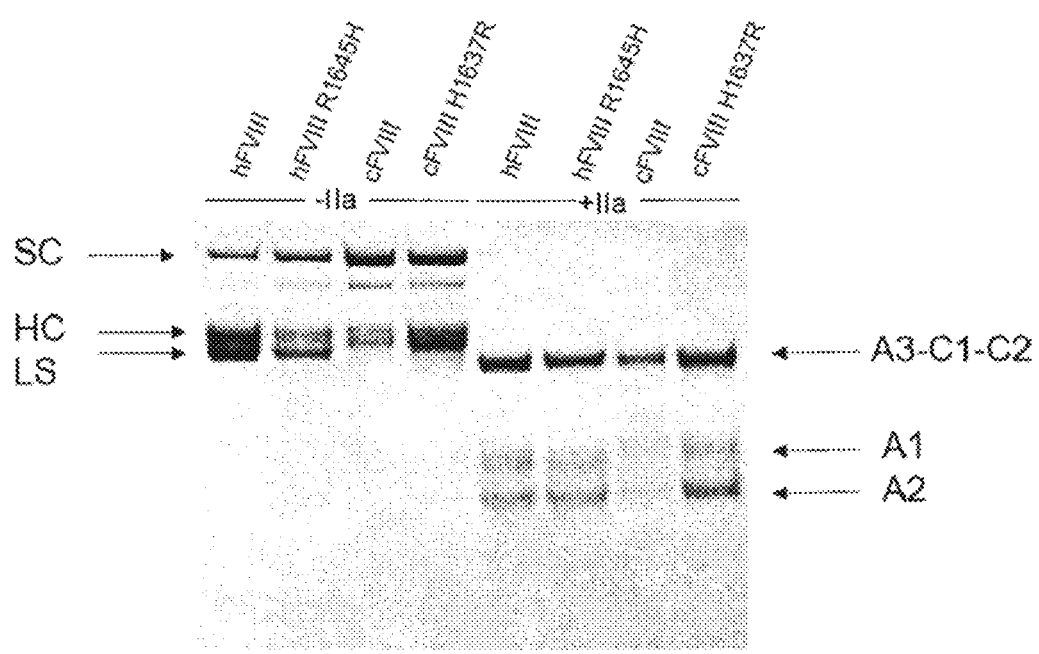
FIG. 5. Human FVIII (WT) or variant FVIII1645H and Canine FVIII (WT) or variant eFVIII H1637R. SDS-PAGE followed by staining with Coomassie blue (left; +thrombin activation–IIa), FVIII-BDD (human or canine; 800 nM) were incubated with IIa (+IIa; 5 nM) for 10 min and the resulting activated FVIII was run on a reducing SDS-PAGE (right, +IIa). The various domains of FVIII are indicated: SC: single chain, HC:heavy chain, LC: light chain, A3-C1-C2 (73 kDa), A1 (50 kDa), and A2 (43 kDa).
Figure 6:
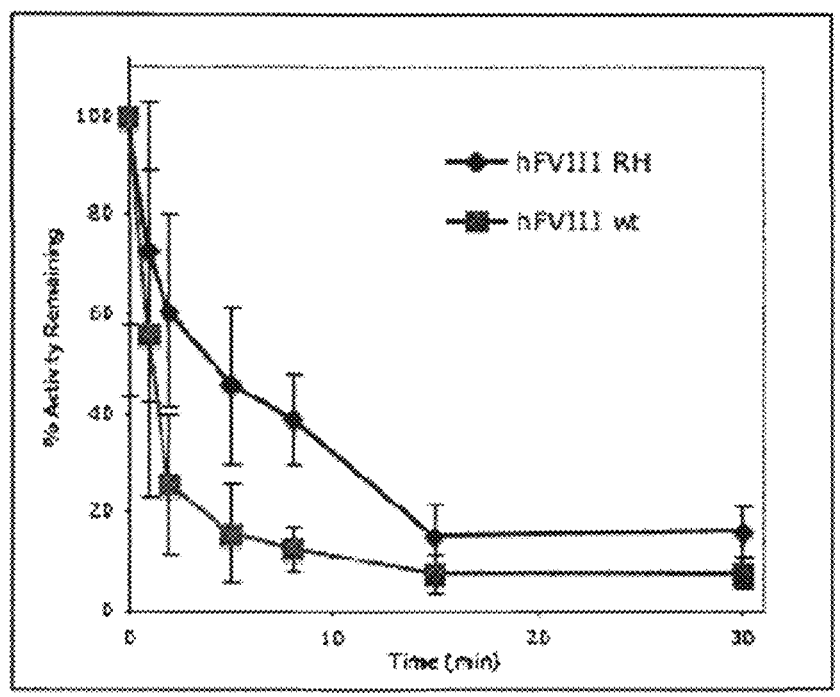
FIG. 6, A2-domain stability of human FVIII (WT) and variant FVIII-RH. The Xase assay was performed by activating 20 nM of hFVIII-BDD forms with 40 nM IIa for 30 seconds at 25° C. The reaction was stopped by adding 60 nM hirudin. At various time points after activation, FVIIIa (0.2 nM, final) was added to the Xase complex [hFIXa (2 nM) hFX (300 nM) and phospholipids (20 µM, phosphatidylcholine/phosphatidylserine; 75:25] and activation was measured by monitoring FXa generation using a chromogenic substrate.

Generation of Mutant Human and Canine FVIII with Modified PACE-Furin Cleavage Sites Using the same techniques described above, we generated human BDD-FVIII with the WT and mutant R1645H proteins. The purified products were run on a SDS-PAGE. The canine FVIII amino acid recognition sequence for intracellular cleavage by PACE/fuin (HHQR) differs from that of human and porcine FVIII (RHQR). We tested the possible role of this cleavage site in increased cFVIII single chain stability and activity. Single substitutions of R→H in human FVIII and H→R at a position homologous in canine FVIII resulted in a shift of ~2-3 fold in the ratio of single chain to cleaved FVIII in the secreted material in the anticipated direction. See FIG. 5. Moreover, the activated HFVIII$^{R1645H}$ had a 3-fold increase in half-life compared to WT hBFVIII. See FIG. 6. Notably, in FIG. 6, the A2 domain dissociation of mutant human FVIII R1645H is similar to that of the wild-type cFVIII and porcine FVIII. These studies suggest a single amino acid substitution at position 1645 enhances human FVIII biological function activity.

Effects of Human FVIII R1650H Variant at Both Micro and Macrocirculation.

Figure 7:
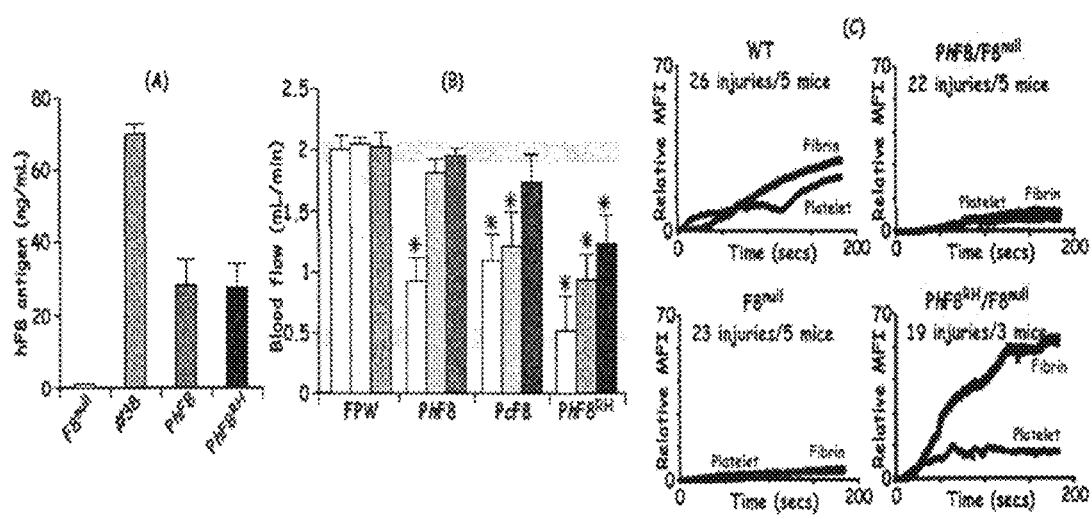
FIG. 7. Studies of PhF8$^{RH}$ Lentivirus. (A) phF8 antigenic level in platelets from F8$^{null}$ mice reconstituted with marrow from line hF8.38/F8$^{null}$ mice (#38) or from F8$^{null}$ mice transfected with either PhF8 or PhF8$^{Rif}$ lentivirus driven by the PF4 promoter (FIG. 2C). (B) FeCl$_3$ carotid artery injury studies of F8$^{null}$ mice reconstituted with marrow transduced with an empty lentivirus FPW or PF4-driven hBF8, cBF8 or hBF8$^{RH}$. Each set of 3 bars go from left (light) to right (dark): 20%, 15%, and 10% FeCl$_3$, 3 min injuries. N=3-5 mice per arm. Mean±2 SE shown. *=p<0.01 compared to FPW. (C) Cremaster arteriole laser injury studies of WT, F8$^{null}$, PhF8/F8$^{null}$ and PhF8$^{RH}$/F8$^{null}$ mice. Fibrin (red) and Plt (green) accumulation over the 3 min is shown. Number of injuries and mice studied are indicated.

As discussed above, canine FVIII has greater activity, in part due to its increased stability as it is expressed as predominantly as a single chain, likely involving a single R1650H (RH) substitution at the PACE/Furin site in cFVIII. Lenti/BMT pFVIII studies expressing phBFVIIIRH showed that the FVIII variant containing this amino acid substitution and B domain deletion was expressed at levels in mice comparable to those observed in transgenic hemophilia A mice expressing wild-type human FVIII. Moreover, the FVIII variant was more efficacious in several bleeding models, including near-normal hemostais in the cremaster laser injury model (microcirculation) or carotid artery model (macrocirculation) in hemophilia A recipient mice. See FIG. 7. This is first lenti/BMT pFVIII-expressing HA mouse with near-normal hemostasis. Preliminary megakaryocyte counts and apoptosis studies show that phBFVIIIRH is not deleterious to megakaryocytes as observed by others when wild-type FVIII was expressed in these cells. These studies provide important new insights into pF8 efficacy for the treatment of hemophilia A.

The hFVIII 1645H variant exhibits higher stability due to the slow dissociation of the A2-domain. Accordingly, this variant may be used to advantage upon tissue injury in order to enhance the generation and duration of clot formation thereby providing a more efficient hemostasis. Additional alterations of the PACE-furin cleavage site should yield similar resistant FVIII variants. Such alterations include, without limitation, deletion of one or more amino acids within the cleavage site, and substitution of the R in the human sequence with an amino acid such as, serine, lysine, methionine, cysteine, proline and tyrosine. Secondly, any of these variants will useful for combining with other forms of FVIII, including, without limitation, IR8 that is resistant to the inactivation by activated protein C. This combination of the hFVIII 1645 (or other PACE-furin resistance forms) with the IR8 variant may further enhance the efficacy of the FVIII in inducing hemostasis. Finally, the protein product described herein could also used for site specific pegylation aimed at increasing the protein half-life or encapsulated with various compounds to enhance efficacy while maintaining appropriate safety parameters.

Figure 8:
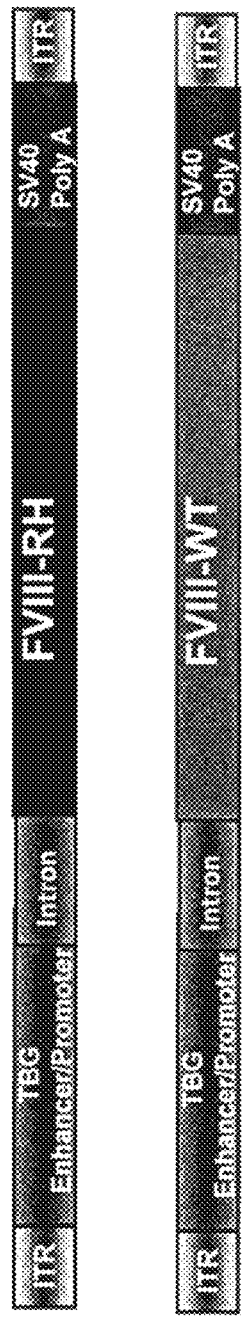
FIG. 8. In vivo In vivo efficacy of plasma hFVIII-HR in severe hemophilia A mice using a mouse model of liver-specific expression by AAV vectors. Constructs utilized for recombinant FVIII-RH (top) and FVIII-WT (bottom).
Figure 9A:
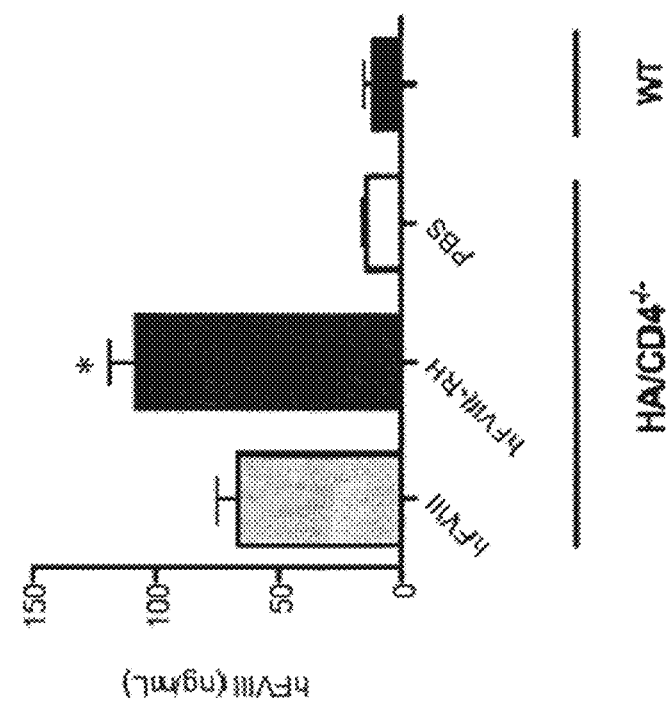
FIG. 9A: Circulating human FVIII-RH and FVIII-WT antigen levels in mice 12 weeks after gene transfer. Control groups: un-treated HA mice and wild-type mice with no human FVIII expression.
Figure 9B:
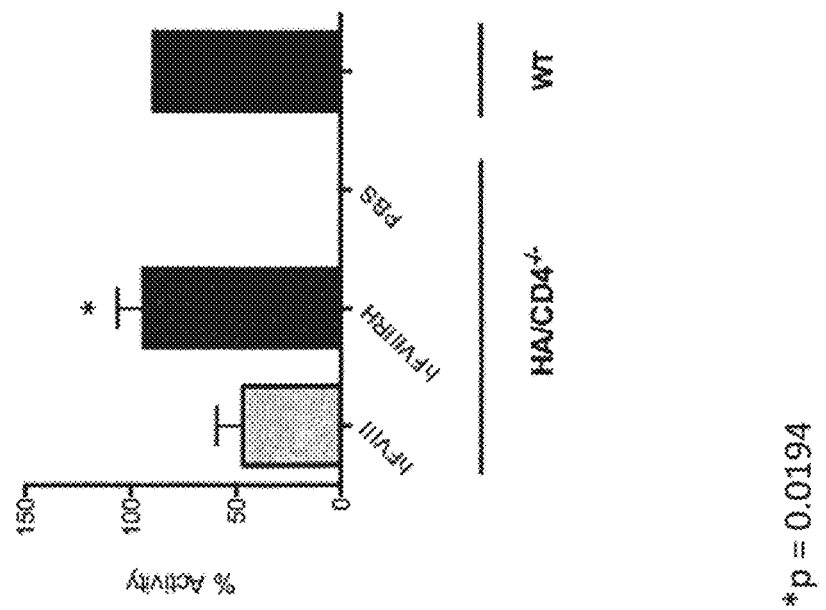
FIG. 9B: Clotting activity of human FVIII-RH and FVIII-WT in mice 12 weeks after gene transfer. Control groups: un-treated HA mice (PBS); Wild-type hemostatically normal mice with no human FVIII expression (WT). Experimental groups: 1) Hemophilia A CD4+ deficient; 2) Hemostatic normal mice (PBS or WT)N=7-8 mice/group; AAV-8: $2\times10^{13}$ vg/kg.

As discussed above, data on expression of human FVIII-RH mutation in the liver of hemophilia A mice demonstrate that at the same vector dose, using adeno-associated viral vector (AAV, FIG. 8) for liver-restricted expression resulted in 50% higher FVIII expression levels compared to the wild-type human FVIII (FVIII-WT), suggesting that this FVIII variant has a higher stability and/or is secreted more efficiently in the plasma (FIG. 9)

Figure 10:
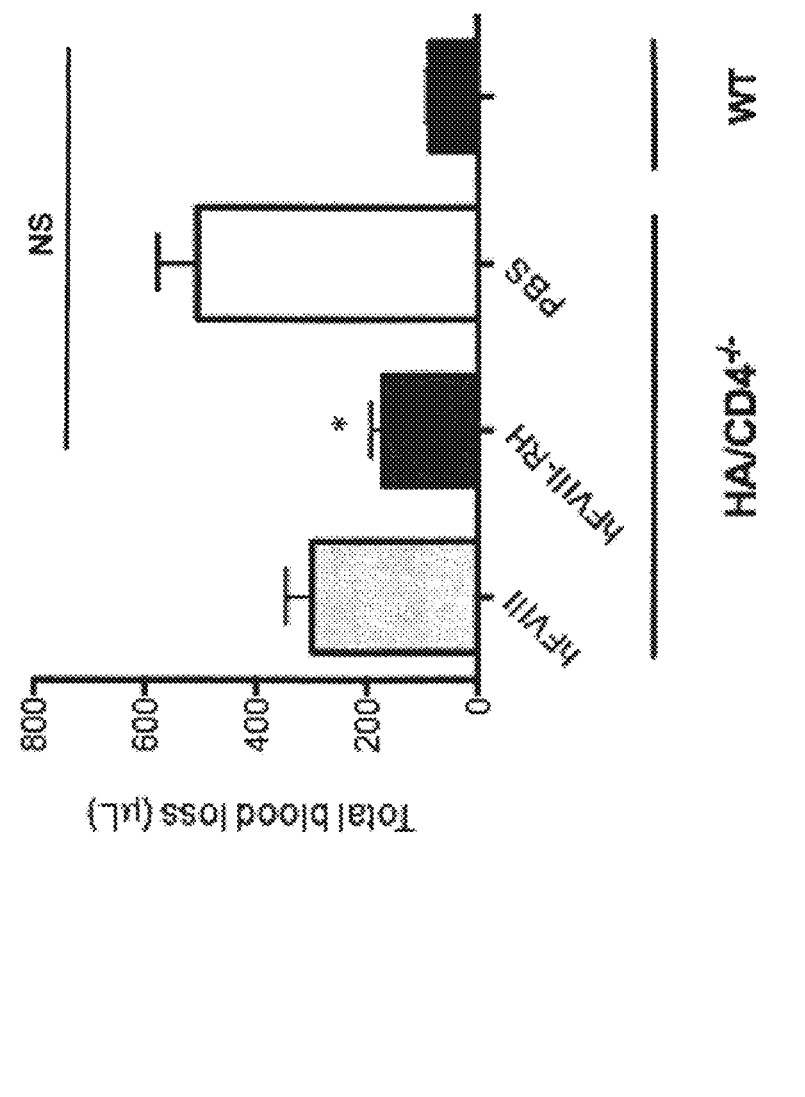
FIG. 10: Normalization of tail bleeding time in human FVIII-RH mice compared to human FVIII-WT in mice 12 weeks after gene transfer. Control groups: PBS-treated HA mice and hemostatic normal WT-mice.

In subsequent experiments, animals expressing FVIII-RH or FVIII-WT underwent to hemostatic challenges and the most informative data is the reduced blood loss to levels compared to hemostastic normal mice. The first time we observed such normal correction (FIG. 10).

In a series of hemostatic challenges at the macrocirculation (carotid artery, FIG. 11) and at microcirculation (cremaster arteriole, ongoing experiments), FVIII-RH proved functional to prevent bleeding at these sites.

Experiments with purified proteins injected exogenously, were associated with formation of stable clotting factor when FVIII-RH was compared to FVIII-WT with minimal dissolution of the clot (as commonly observed with FVIII-WT).

Figure 12B:
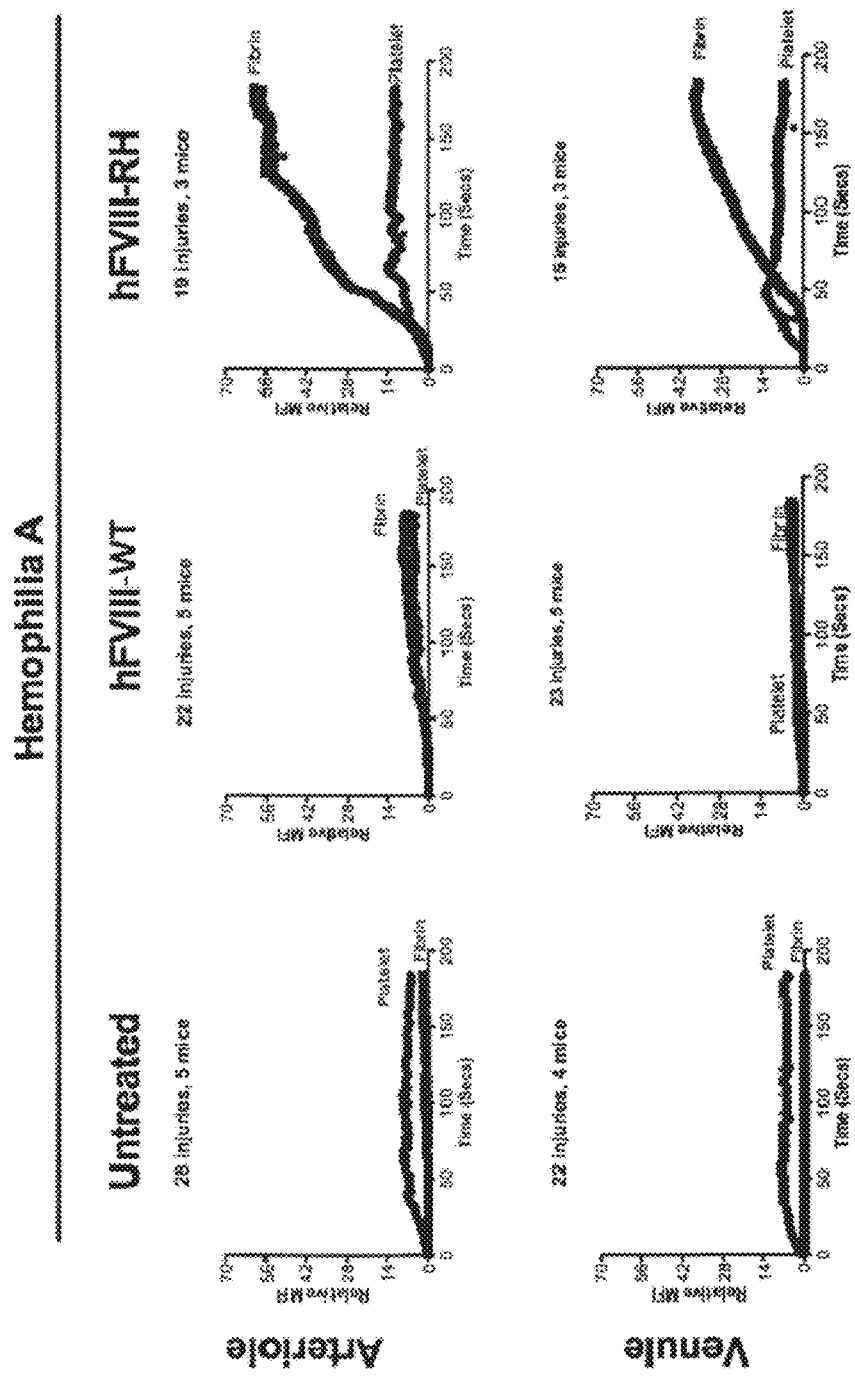
FIG. 12B shows the results obtained from lentiviral mediated platelet restricted expression of human FVIIIRH on in vivo thrombus formation occurring via laser-induced injury.

In a different experimental system; FVIII-RH was expressed specifically in the platelet and its efficacy tested in the cremaster arteriole injury model (FIG. 12A). Two unexpected observations were finding: (1) FVIII-RH resulted in stable clot (unpublished), as observed in the transgenic mice with the highest expression levels (FIG. 12B) (see Blood 2011 for the FVIII-WT and not for the variant RH), (2) the accumulation of fibrin in this model, surpassed that of hemostatic normal mice, which suggest that local increase of FVIII-RH upon platelet activation has a potent hemostatic effect (FIG. 12C).

In summary, using distinct models of expression of FVIII-RH in the plasma (derived from liver by AAV vector) or by injection of purified protein, provide further support for the use of this variant in clinics. Secondly, expression of FVIII-RH in platelet provides strong evidence that local increment of the protein has a potent procoagulant effect. Accordingly, the best performing FVIII variant(s) can be used for (a) protein production for the treatment of bleeding, either prophylatically or in response to a bleed, (b) in transgenes for direct gene delivery by viral or non-viral vectors to the liver, skeletal muscle, or skin. In addition, these vectors and lentiviral, retroviral vectors can be employed to target hematopoietic stem cell for expression in cells from the bone marrow. They can also be utilized to drive expression of variant FVIII in induced Progenitor cells (iPS) or human or non-human embryonic stem cells. Such cells can be transduced ex vivo and then returned to the patient via IV or local injection. In one approach, the cells are derived from the patient. In another, the cells may be obtained from an immunologically compatible donor.

REFERENCES

1. Nichols T C, Dillow A M, Franck H W, et al. Protein replacement therapy and gene transfer in canine models of hemophilia A, hemophilia B, von Willebrand disease, and factor VII deficiency, Ilar J. 2009; 50:144-167.
2. Lakich D, Kazazian H H, Antonarakis S E, Gitschier J. Inversions disrupting the factor VIII gene as a common cause of severe haemophilia A. Nature Genet. 1993; 5:236-241.
3. Graham, J B, Buckwalter J A, Hartley L J, Brinkhous K M. Canine hemophilia: Observations on the course, the clotting anomaly, and the effects of blood transfusion. J Exp Med. 1949; 90:97-102.
4. Lozier J N, Dutra A, Pak E, et al. The Chapel Hill hemophilia A dog colony exhibits a factor VIII gene inversion. Proc Natl Acad Sci USA. 2002; 99:12991-12996.
5. Cameron C, Notley C, Hoyle S, et al. The canine factor VIII cDNA and 5' flanking sequence. Thromb Haemost. 1998; 79:317-322.
6. Viel K R, Ameri A, Abshire T C, et al. Inhibitors of factor VIII in black patients with hemophilia. N Engl J Med. 2009; 360:1618-1627.
7. Sarkar R, Tetreault R, Gao G, et al. Total correction of hemophilia A mice with canine FVIII using an AAV 8 serotype. Blood. 2004; 103:1253-1260.
8. Cao W, Krishnaswamy S, Camire R M, Lenting P J, Zheng X L. Factor VIII accelerates proteolytic cleavage of von Willebrand factor by ADAMTSI3. Proc Natl Acad Sci USA. 2008; 105:7416-7421.
9. Kaufman R J, Davies M V, Wasley L C, Michnick D. Improved vectors for stable expression of foreign genes in mammalian cells by use of the untranslated leader sequence from EMC virus. Nucleic Acids Res. 1991; 19:4485-4490.
10. Toso R, Camire R M, Removal of B-domain sequences from factor V rather than specific proteolysis underlies the mechanism by which cofactor function is realized. J Biol Chem. 2004; 279:21643-21650.
11. Doering C, Parker E T, Healey J F, Craddock H N, Barrow R T, Lollar P. Expression and characterization of recombinant murine factor VIII. Thromb Haemost. 2002; 88:450-458.
12. Lollar P, Parker E T, Fay P J. Coagulant properties of hybrid human/porcine factor VIII molecules. J Biol Chem. 1992; 267:23652-23657.
13. Arruda V R, Hagstrom J N, Deitch J, et al. Posttranslational modifications of recombinant myotube-synthesized human factor IX, Blood. 2001; 97:130-138.
14. Herzog R W, Mount J D, Arruda V R, High K A, Lothrop C D, Jr. Muscle-directed gene transfer and transient immune suppression result in sustained partial correction of canine hemophilia B caused by a null mutation, Mol Ther. 2001; 4:192-200.
15. Brinkhous K M, Sandberg H, Garris J B, et al. Purified human factor VIII procoagulant protein: comparative hemostatic response after infusions into hemophilic and von Willebrand disease dogs. Proc Natl Acad Sci USA. 1985; 82:8752-8756.
16. Brinkhous K M, Hedner U, Garris J B, Diness V, Read M S. Effect of recombinant factor VIIa on the hemostatic defect in dogs with hemophilia A, hemophilia B, and von Willebrand disease. Proc Natl Acad Sci USA. 1989; 86:1382-1386.
17. Doering C B, Healey J F, Parker E T, Barrow R T, Lollar P. High level expression of recombinant porcine coagulation factor VIII. J Biol Chem. 2002; 277:38345-38349.
18. Shibata M, Rowle F, Labelle A, et al. Characterization of recombinant canine FVIII and quantitative determination of factor FVIII in canine plasma. J Thromb Haemost. 2005; 3:P0033.
19. Brinkhous K, Sandberg H, Widlund L, et al. Preclinical pharmacology of albumin-free Bdomain deleted recombinant factor VIII. Semin. Thromb Hemost. 2002; 28:269-272.
20. Connelly S, Mount J, Mauser A, et al., Complete short-term correction of canine hemophilia A by in vivo gene therapy. Blood. 1996; 88:3846-3853.
21. Brown B D, Shi C X, Powell S, Hurlbut D, Graham F L, Lillicrap D, Helper-dependent adenoviral vectors mediate therapeutic factor VIII expression for several months with minimal accompanying toxicity in a canine model of severe hemophilia A, Blood. 2004; 103:804-810.
22. Chuah M K, Schiedner G, Thorrez L, et al. Therapeutic factor VIII levels and negligible toxicity in mouse and dog models of hemophilia A following gene therapy with high-capacity adenoviral vectors. Blood. 2003; 101:1734-1743.
23. Jiang H, Lillicrap D, Patarroyo-White S, et al. Multiyear therapeutic benefit of AAV serotypes 2, 6, and 8 delivering factor VIII to hemophilia A mice and dogs. Blood. 2006; 108:107-115.
24. McCormack W M, Jr., Seiler M P, Bertin T K, et al. Helper-dependent adenoviral gene therapy mediates long-term correction of the clotting defect in the canine hemophilia A model. J Thromb Haemost. 2006; 4:1218-1225.

While certain of the preferred embodiments of the present, invention have been described and specifically exemplified above, it is not intended that the invention be limited to such embodiments. Various modifications may be made thereto without departing from the scope and spirit of the present invention, as set forth in the following claims.

What is claimed is:

1. An isolated recombinant nucleic acid encoding a FVIII variant having a modified PACE/furin cleavage site and a B domain deletion (BDD) for modulating hemostasis, said human PACE/furin cleavage site consisting of amino acids RHQR, said FVIII variant being a human variant selected from the group consisting essentially of:
  i) a FVIII variant with said BDD and wherein R is substituted with an H in the PACE/furin cleavage site;
  ii a FVIII variant with said BDD and wherein one amino acid at said PACE/furin cleavage site is deleted;
  iii) a FVIII variant with said BDD and wherein R at said cleavage site is substituted with an amino acid selected from the group consisting of a serine, lysine, methionine, cysteine, proline and tyrosine; and
  iv) a FVIII variant wherein one or more amino acids at said PACE/furin cleavage site and a B domain are deleted, each of i), ii), iii), and iv) exhibiting increased specific activity and stability relative to human FVIII-BDD lacking said substitution and deletions.

2. An expression vector comprising the nucleic acid of claim 1.

3. The vector of claim 2, selected from the group consisting of an adenoviral vector, an adeno-associated virus (AAV) vector, a retroviral vector, a plasmid, and a lentiviral vector.

4. A method for treatment of a hemostasis related disorder in a patient in need thereof comprising administration of a therapeutically effective amount of the vector of claim 3 in a biologically acceptable carrier, wherein said vector is an adeno associated virus (AAV) vector.

5. The method of claim 4, wherein said FVIII variant is a pro-coagulant and said disorder is selected from the group consisting of hemophilia A, von Willebrand diseases and bleeding associated with trauma, injury, thrombosis, thrombocytopenia, stroke, coagulopathy, disseminated intravascular coagulation (DIC) and over-anticoagulation treatment disorders.

6. The method of claim 4 or claim 5, wherein said FVIII variant is encapsulated in a liposome or mixed with phospholipids or micelles.

7. A host cell expressing the FVIII variant encoded by the nucleic acid of claim 1.

8. The nucleic acid encoding the FVIII variant as claimed in claim 1, wherein R at said cleavage site is substituted with an amino acid selected from the group consisting of a serine, lysine, methionine, cysteine, proline and tyrosine.

9. The nucleic acid encoding the FVIII variant as claimed in claim 1, wherein at least one amino acid at said PACE/furin cleavage site is deleted.

10. The nucleic acid encoding the FVIII variant of claim 1, wherein two of the amino acids at the PACE/Furin cleavage site are deleted.

11. The nucleic acid encoding the FVIII variant of claim 1, wherein three of the amino acids at the PACE/Furin cleavage site are deleted.

12. The nucleic acid encoding the FVIII variant of claim 1, wherein all four of the amino acids at the PACE/Furin cleavage site are deleted.

13. An adeno associated virus (AAV) vector comprising the nucleic acid of claim 1.

14. The adeno associated virus (AAV) vector of claim 13, further comprising ITR (inverted terminal repeat) elements.

* * * * *